(12) United States Patent
Gronli

(10) Patent No.: US 6,548,814 B1
(45) Date of Patent: Apr. 15, 2003

(54) ARRANGEMENT AND A METHOD FOR MEASURING LEVEL, INTERFACE LEVEL AND DENSITY PROFILE OF A FLUID IN TANKS OR CONTAINERS

(75) Inventor: Bjorn Gronli, Drammen (NO)

(73) Assignee: BTG Källe Inventing AB (SE)

( * ) Notice: Subject to any disclaimer, the term of this patent is extended or adjusted under 35 U.S.C. 154(b) by 0 days.

(21) Appl. No.: 09/508,839

(22) PCT Filed: Sep. 16, 1998

(86) PCT No.: PCT/SE98/01666

§ 371 (c)(1),
(2), (4) Date: Jun. 1, 2000

(87) PCT Pub. No.: WO99/17085

PCT Pub. Date: Apr. 8, 1999

(30) Foreign Application Priority Data

Sep. 17, 1997 (SE) ............................................... 9703360

(51) Int. Cl.[7] ............................................. G01F 23/288
(52) U.S. Cl. .................................. 250/357.1; 250/366
(58) Field of Search ............................. 250/357.1, 366, 250/363.09

(56) References Cited

U.S. PATENT DOCUMENTS

| 3,098,154 A | 7/1963 | Crump ....................... 250/43.5 |
| 3,895,232 A | * 7/1975 | Schneeberger ................ 250/366 |
| 4,079,257 A | * 3/1978 | Jatteau et al. ............. 250/252.1 |
| 4,471,223 A | * 9/1984 | Hurst et al. ............... 250/357.1 |
| 4,520,266 A | 5/1985 | Fletcher et al. ............ 250/357.1 |
| 4,611,117 A | 9/1986 | Seibert et al. ............. 250/252.1 |
| 4,870,280 A | * 9/1989 | Yamashita et al. ......... 250/363.01 |
| 5,004,904 A | * 4/1991 | Yamakawa et al. ............ 250/207 |
| 5,218,202 A | 6/1993 | Evers ........................ 250/252.1 |

FOREIGN PATENT DOCUMENTS

| DE | 19722837 A1 | 12/1998 | |
| EP | 0060630 A2 | 9/1982 | |
| GB | 2326232 A | * 12/1998 | ......... G01F/23/288 |
| JP | 02074827 A | * 3/1990 | ........... G01F/23/28 |

* cited by examiner

Primary Examiner—Constantine Hannaher
(74) Attorney, Agent, or Firm—Ostrolenk, Faber, Gerb & Soffen, LLP

(57) ABSTRACT

The invention is an apparatus and method for measuring a level, an interface level, and/or a density profile of at least one fluid in a container (2, 3) with at least two nuclear radiation sources (9) vertically arranged at a predetermined distance from each other inside or both inside and outside the tank. A defector unit (11) is used and includes a scintillator rod (12) with photo multiplier tubes (13) at each end. Electronic means provides information on fluid level positions and radiation levels at different places along the scintillator rod (12) by measuring pulse amplitudes from the photo multiplier tube. The radiation is converted to electric pulses having an amplitude proportionate to the light intensity of the radiation at the actual position along the rod (12). A ratiometric calculation of the amplitude determines the position of the corresponding radiation quant.

8 Claims, 2 Drawing Sheets

Figure 1:
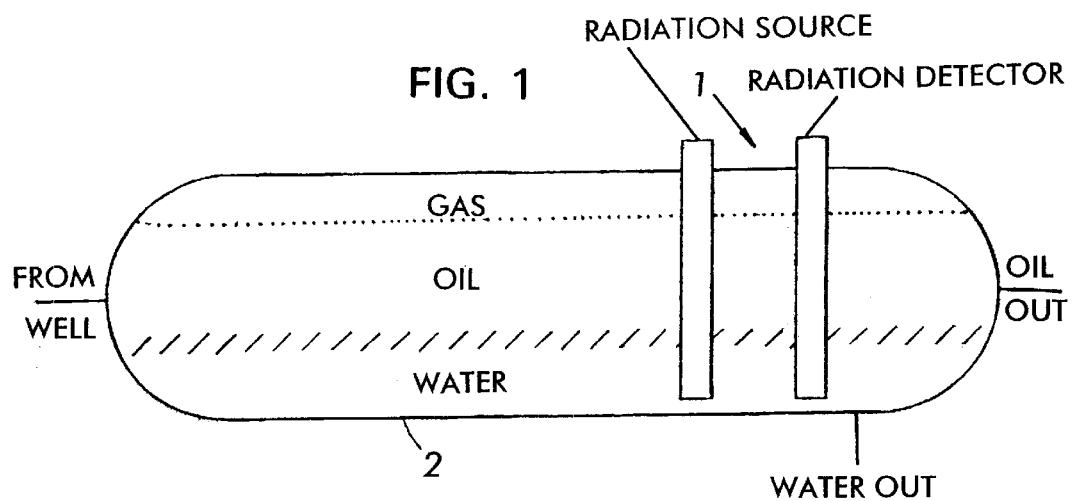

ARRANGEMENT AND A METHOD FOR MEASURING LEVEL, INTERFACE LEVEL AND DENSITY PROFILE OF A FLUID IN TANKS OR CONTAINERS

In many industrial processes there is a need of one or more measurements of level, i.e. the vertical position of the surface of a fluid; interface level, i.e. the vertical position of the layer between two fluids; and density profile, i.e. the density of fluids as a function of the height measured at discrete points or continuously along a vertical axis; in tanks to enable automatic control of the related operation. For certain processes the measurement may be very hard or impossible to carry out. Some factors that make this measurement difficult can be harsh or inaccessible environments, aggressive or dangerous fluids and/or liquids, high pressure or temperatures, fluids causing deposits inside the tank/container, and so on. One example of a process that involves several of these problems is in sub-sea oil separator tanks. A nucleonic system is one method of measurement in this type of separator tanks.

In the technique previously known one usually uses a vertical array of several gamma radiation sources and a vertical array of several radiation detectors positioned at a suitable distance from each other. The sources and the detectors are normally inserted in two separate protection pipes. The two pipes are mounted either both inside the tank or one inside and the other outside it. The gamma radiation sources are also shielded by lead with openings towards the detectors. Horizontal radiation beams from the gamma sources are pointed at each of the detectors. The attenuation of the radiation beam passing through the actual fluids, i.e. the gas and/or liquids, will vary depending on the amount of gas and the density of the liquid. A higher density will cause more attenuation and lower signals from the detector. In this way the detector signals along the vertical axis represent a function of the density profile. Differences in adjacent detector signals indicate a fluid surface or interface level at that position. Instead of an array of radiation detectors, it is possible to use one long vertical detector according to the present invention having associated electronics that can separate the radiation the different beams. In both cases scintilliation detectors could be used. The array of separate gamma radiation sources could be replaced by one vertical wire source.

The problems when using an array of PTM detectors, i.e. a scintillator with an attached photo multiplier tube, are that the reliability of the system will be reduced and the costs will increase for large tanks or containers because of the fact that a large number of parts will be needed. This also limits the height resolution because of the size of the detectors and the maximum number that is practical. By the expression "scintillator" is meant a material that emits light flashes when exposed to nuclear radiation, preferably gamma radiation. It typically consists of plastic or crystal for industrial applications.

The object of the present invention is to provide an arrangement of the type mentioned in the introduction, whereby the drawbacks existing in previously known technique are eliminated. The characterizing features are set forth in the accompanying claims.

According to the invention there is proposed a solution with a long detector unit comprising a long scintillator rod with associated photo multiplier tubes covering the total height used instead of the array of PMT detectors. The long detector unit has a PMT, i.e. a photo multiplier tube, constituted by a photo detector, which is very sensitive to light, at each end and associated electronics that provides both information on position as well as radiation level at the different positions along the detector unit.

Figure 2:
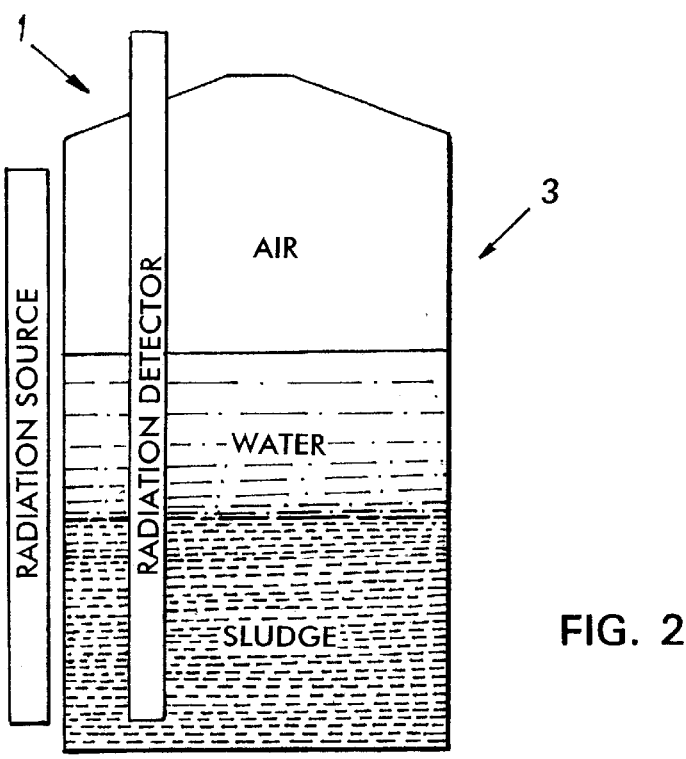
Figure 3:
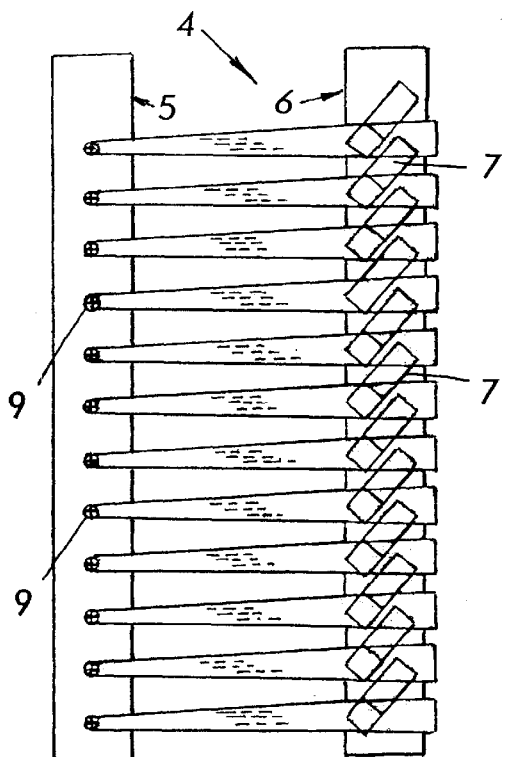
Figure 4:
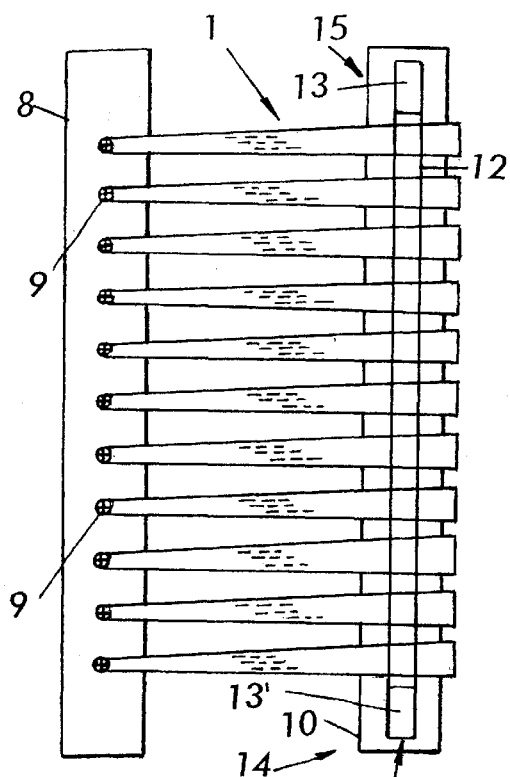
Figure 5:
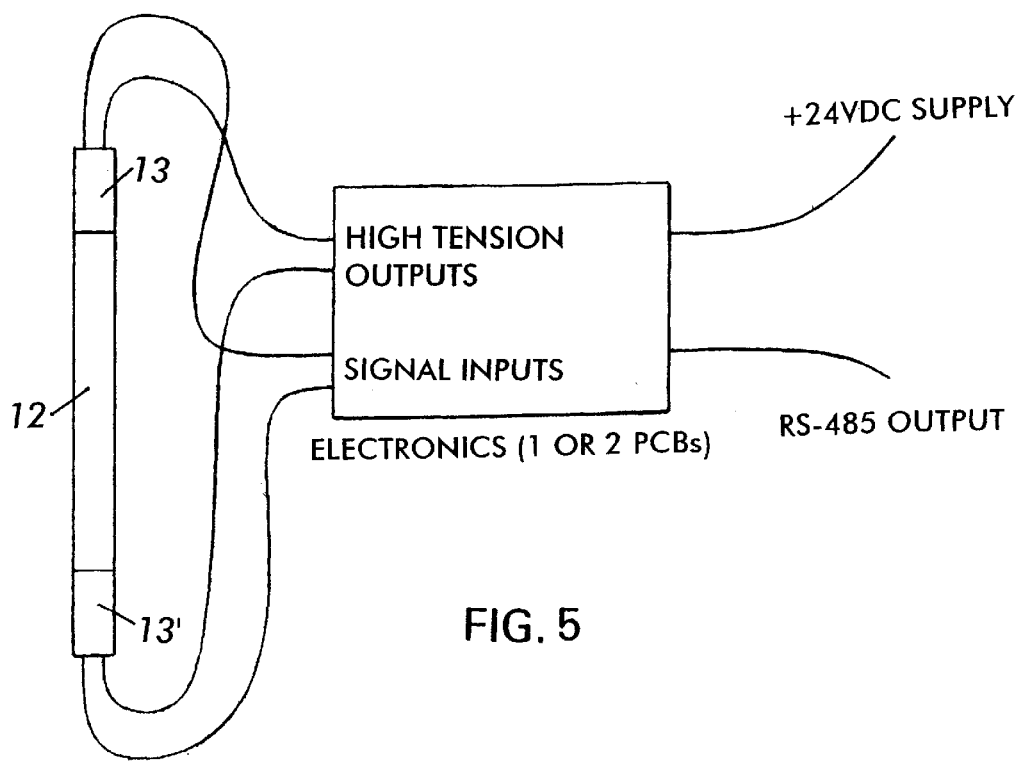

The invention will be described more in detail below by the aid of preferred embodiments, reference being made to the accompanying drawings, in which FIG. 1 schematically shows a cross-section through a tank intended to be placed as a sub-sea separator and which contains water, oil and gas and is provided with a measurement arrangement according to the invention, FIG. 2 schematically shows a cross-section through a sludge tank containing sludge, water and air, in which a measurement arrangement according to the invention is used for determining level and density profile of the different media, FIG. 3 schematically shows a known measurement arrangement, where an array of radiation detectors is used in the detector unit, FIG. 4 schematically shows the measurement arrangement according to the present invention, where the detector unit consists of a long detector rod having a photo multiplier tube at each end, and FIG. 5 shows a block diagram for a detector rod system according to the invention.

As appears from FIGS. 1 and 2 there are here illustrated two fields of application for the measurement arrangement 1 according to the invention, namely e.g. in a sub-sea separator tank or container 2 and in a sludge tank 3.

In FIG. 3 there is illustrated a previously known measurement arrangement 4 comprising a radiation source 5 and a radiation detector unit 6, the latter of which comprises an array of radiation detectors 7.

FIG. 4 illustrates the measurement arrangement 1 according to the invention comprising radiation sources 9, e.g. gamma radiation sources, inserted in a protection pipe 8 and a detector unit 11 inserted in another separate protection pipe 10, the detector unit 11 covering the total height used. The detector unit 11 comprises a long scintillator rod 12 with a PMT or photo multiplier tube 13, 13' fixed at each end 14 and 15. The scintillator rod 12 consists, as mentioned above, of a photo detector, which is very sensitive to light, with a structure and associated electronics, which provide information both on position as well as radiation level at different positions along the scintillator rod 12.

A special signal processing is, however, needed to obtain information on both position as well as radiation level at the different positions along the long detector unit 11. This is achieved by attaching a PMT, e.g. a photo multiplier tube 13, 13', to each end of the long scintillator rod 12. The scintillator material consists of special plastic and the material, as well as the surface treatment are made to provide a suitable light attenuation along the length of the scintillator rod 12. The interaction between the radiation and the scintillator rod 12 is caused by single radiation quants being absorbed in the plastic and producing a light flash. Depending on the position in the scintillator rod 12, where the radiation quant is absorbed, the light has a certain distance to travel before it reaches each of the photo multiplier tubes 13, 13'. During this travel the light is attenuated. Each photo multiplier tube 13, 13' emits an electric pulse of amplitude proportional to the intensity of the light at that end. The pulses from each of the photo multiplier tubes will occur simultaneously. The more the light is attenuated during the travel in the scintillator rod 12, the lower is the pulse amplitude of the photo multiplier tube. If the detection is in the middle of the length of the scintillator rod 12, the pulse amplitude of the two simultaneous pulses will be equal. If the detection is at the end of the length of the scintillator rod 12, the pulse amplitude will be high at the near end and low at the far end. An electronics measures the amplitude of the two simultaneous pulses and makes a ratiometric calculation to determine the position of the corresponding radiation quant. The rate of quants being absorbed by the scintillator rod 12 is proportional to the radiation intensity. Consequently, the pulse rate from the photo multiplier tubes respresents the radiation intensity. By incrementing a position buffer in the memory of the electronics corresponding to the position of each quant being absorbed in the scintillator rod 12, the intensity and the radiation are measured at small discrete steps along the detector unit 11.

Since the photo multiplier tubes 13, 13' are inherently unstable devices, they need to be controlled by feed-back to produce a sufficiently accurate signal in industrial applications. The normal way of control for smaller detectors is to do some type of analysis by comparing the pulse heights. In a long detector unit, where the pulse heights change when the level of the fluid or liquid in the process changes, this method of stabilization will not work well. Three ways will be mentioned below, by means of which this problem is solved in accordance with the invention, namely:

1. A small reference radiation source (isotope) is attached directly to the scintillator rod 12. The pulse height from various isotopes depends on the type of radiation. The type of reference source and the mounting on the scintillator rod 12 are chosen to get higher pulses than that from the radiation passing through the fluid. The electronics extracts the higher pulses by pulse height discriminators and uses that in a feedback to control the photo multiplier tubes 13, 13'.
2. A light-emitting diode (LED) is attached directly to the scintillator rod 12. The light-emitting diode is pulsed and the pulses are extracted by the electronics by pulse height discriminators and used as feedback to control the photo multiplier tubes 13, 13'.
3. Two pipes are mounted horizontally between the radiation sources and the long photo multiplier tube detector unit each near the top and the bottom. This prevents the fluid from attenuating the radiation and, therefore, the intensity of the radiation will be constant near the ends of the detector unit. The radiation near the end will produce the highest pulses at that end. The electronics extracts the higher pulses by pulse height discriminators and uses that in a feedback to control the photo multiplier tubes.

Cross-coupling from adjacent radiation beams causes an error in the measured density due to scattering of the gamma radiation. Some of the scattered radiation will hit the adjacent detectors. The most significant error occurs when the beam above is penetrating lighter liquid or gas than the measured beam.

To overcome this problem a more accurate density is determined at each discrete position with the following algorithm:

In e.g. position 4: $ro = k0 + k1*x3 + k2*x3^2 + k3*x4 + k4*x4^2$, where ro is the density, x3 is the signal in position 3, x4 is the signal in position 4 and the indexes are numbered from the top and down, x1 being the signal at the top and xn at the lowest point of the detector and k0, k1, k2, k4 are calibration constants and are determined by multiple regression after measuring all the signals x1, x2, . . . with a number of different densities. The other positions are made in the same way.

An array of PMT or PIN detectors has a limited height resolution due to the discrete measurement positions of the detectors and a long PMT detector has a limited height resolution due to the discrete positions of the radio sources. This has been solved in the following manner. An improved height resolution is obtained according to the invention by a special radiation beam geometry and corresponding signal processing. Each radiation beam is made wide enough to partially overlap the beam on each side. In the case of an array of photo multiplier tube detectors the signal from each detector represents discrete positions along the vertical axis. In the case of a long photo multiplier tube detector the detector signal is divided into discrete intervals along the vertical axis. A more accurate level is determined at each discrete position with the following algorithm:

In e.g. position 3: $y = k0 + k1*x3 + k2*x3^2 + k3*x4 + k4*x4^2$, where y is the more accurate height, x3 is the signal in position 3, x4 is the signal in position 4 and the indexes are numbered from the top and down, x1 being the signal at the top and xn at the lowest point of the detector unit and k0, k1, k2, k3, k4 are calibration constants and are determined by multiple regression after measuring all the signals x1, x2, . . . with a number of different fluid levels. The other positions are made in the same way.

What is claimed is:

1. An apparatus for selectively performing one or more measurements of a level, an interface level and a density profile of at least one fluid located in a container comprising:

a nuclear radiation source located inside of a fire protection pipe;

a nuclear radiation detector unit located inside of a second protection pipe, the nuclear radiation detector unit covers a total height of the container, the first protection pipe and the second protection pipe are vertically mounted on the container at a suitable distance from each other;

a long vertical detector including a scintillator rod that has a photo multiplier tube fixed to each end, the long vertical detector is located in the nuclear radiation detector unit; and an electronic means that calculates at least a position and a radiation level of a radiation quant at any position along the scintillator rod by measuring an amplitude of each of two electric pulses that are simultaneously emitted from each of the photo multiplier tubes upon an absorption of the respective radiation quant into the scintillator rod.

2. The apparatus according to claim 1, wherein the scintillator rod includes a plastic or crystal and a surface of the scintillator rod is treated to provide a suitable light attenuation along the scintillator rod.

3. A method for selectively performing one or more measurements of a level, an interface level, and a density profile of at least one fluid located in a container comprising:

providing a nuclear radiation source and a nuclear radiation detector unit that covers a total height of the container, the nuclear radiation detector unit comprises a long vertical detector in the form of a scintillator rod that has a photo multiplier tube fixed to each end;

inserting the nuclear radiation source into a first protective pipe;

inserting the nuclear radiation detector unit into a second protective pipe;

mounting vertically the first protection pipe and the second protection pipe onto the container at a suitable distance from each other;

absorbing a radiation quant from the nuclear radiation source into the scintillator rod;

transforming the absorbed radiation quant into an electric pulse that has an amplitude proportional to an intensity of the radiation quant at a respective position along the scintillator rod;

measuring electronically the amplitude of two simultaneous electric pulses; and determining electronically the respective position along the scintillator rod of the absorbed radiation quant by a ratiometric calculation.

4. The method according to claim 3, further comprising:

selecting a small reference radiation source in the form of an isotope that will produce a suitable electric pulse height with respect to a type of radiation produced by the nuclear radiation source;

mounting the small reference radiation source directly to the scintillator rod at a position on the scintillator rod that will produce an electric pulse height greater than an electric pulse height produced by a plurality of radiation quants that are emitted from the nuclear radiation source and are passed through the fluid;

extracting electronically the higher electric pulses by use of an electric pulse height discriminator unit; and controlling the photo multiplier tubes by feedback of the extracted higher electric pulses to produce a sufficiently accurate signal.

5. The method according to claim 3, further comprising:

mounting a light-emitting diode directly to the scintillator rod;

pulsing the light-emitting diode;

extracting electronically a plurality of electric pulses emitted by light-emitting diode by use of an electric pulse height discriminator unit; and controlling the photo multiplier tubes by feedback of the extracted electric pulses of the light-emitting diode to produce a sufficiently accurate signal.

6. The method according to claim 3, further comprising:

preventing the fluid from attenuating a plurality of radiation quants emitted by the nuclear radiation source by mounting horizontally a first pipe from the top end of the nuclear radiation detector unit to the nuclear radiation source and mounting horizontally a second pipe from the bottom end of the nuclear radiation detector unit to the nuclear radiation source, so that an intensity of a plurality of radiation quants absorbed at each end of the scintillation rod is constant;

extracting electronically the electric pulses produced by the plurality of radiation quants absorbed at each end of the scintillation rod by use of an electric pulse height discriminator unit; and controlling the photo multiplier tubes by feedback of the extracted electric pulses to produce a sufficiently accurate signal.

7. The method according to claim 3, further comprising:

determining the fluid density profile at each discrete position along the scintillator rod with the following algorithm:

in e.g. position 4: $r_o = k_0 + k_1(x_3) + k_2(x_3)^2 + k_3(x_4) + k_4(x_4)^2$, where $r_o$ is the fluid density, $x_3$ is the electric pulse of the absorbed radiation quant in position 3, $x_4$ is the electric pulse of the absorbed radiation quant in position 4, and the indexes are numbered from the top and down, $x_1$ being the electric pulse of the absorbed radiation quant at the top of the nuclear radiation detector unit in position 1 and $x_n$ being the electric pulse of the absorbed radiation quant at the point of the nuclear radiation detector unit in position n, and $k_0$, $k_1$, $k_2$, $k_3$, and $k_4$ are calibration constants that are determined by multiple regression after measuring the electric pulses, $x_1$, $x_2$, $x_3$, ... $x_n$, of the absorbed radiation quants with a number of different densities.

8. The method according to claim 3, wherein an improved height resolution of the radiation quants from the radiation source is obtained by a geometry-specific radiation beam and corresponding signal processing, where each radiation quant is wide enough to partially overlap a radiation quant on each side, whereby an electric pulse measured at each of a plurality of discrete positions on the vertical axis of the scintillator rod is divided into discrete intervals along the vertical axis of the scintillator rod concurrently as a more accurate level is determined at each discrete position on the vertical axis of the scintillator rod with the following algorithm:

in e.g. position 3: $y = k_0 + k_1(x_3) + k_2(x_3)^2 + k_3(x_4) + k_4(x_4)^2$, where y is the more accurate height, $x_3$ is the electric pulse of the absorbed radiation quant in position 3, $x_4$ is the electric pulse of the absorbed radiation quant in position 4, and the indexes are numbered from the top and down, $x_1$ being the electric pulse of the absorbed radiation quant at the top of the nuclear radiation detector unit in position 1 and $x_n$ being the electric pulse of the absorbed radiation quant at the point of the nuclear radiation detector unit in position n, and $k_0$, $k_1$, $k_2$, $k_3$, and $k_4$ are calibration constants that are determined by multiple regression after measuring the electric pulses, $x_1$, $x_2$, $x_3$, ... $x_n$, of the absorbed radiation quants with a number of different densities.

* * * * *